United States Patent [19]

Ohkuma et al.

[11] 4,323,577
[45] Apr. 6, 1982

[54] AQUEOUS SOLUTION OF NITROGLYCERIN

[75] Inventors: Takaaki Ohkuma, Tokyo; Hiroshi Ninomiya, Sayama; Masaaki Nakamura, Ageo; Genichi Idzu, Yono, all of Japan

[73] Assignee: Nippon Kayaku Kabushiki Kaisha, Tokyo, Japan

[21] Appl. No.: 203,142

[22] Filed: Nov. 3, 1980

[30] Foreign Application Priority Data

Nov. 13, 1979 [JP] Japan ................................ 54-146011

[51] Int. Cl.³ .............................................. A61K 31/21
[52] U.S. Cl. ...................................... 424/298; 260/457
[58] Field of Search ................. 424/349, 298; 260/457

[56] References Cited

U.S. PATENT DOCUMENTS 3,155,574  11/1964  Silson et al. ........................... 424/45

FOREIGN PATENT DOCUMENTS 1343347  1/1974  United Kingdom .
1427881  3/1976  United Kingdom .
1516359  7/1978  United Kingdom .

OTHER PUBLICATIONS

Chem. Abstr. 23:236d (1929).
Chem. Abstr. 29:4516q–4517 (1935).
Chem. Abstr. 84: entry 8908g (1976).

Primary Examiner—Frank Cacciapaglia, Jr.
Attorney, Agent, or Firm—Henry C. Nields

[57]  ABSTRACT

An aqueous solution of nitroglycerin comprising at least one substance selected from among sorbitol, mannitol and xylitol in addition to nitroglycerin, and having a high degree of stability for storage.

4 Claims, No Drawings

AQUEOUS SOLUTION OF NITROGLYCERIN

BACKGROUND OF THE INVENTION

1. Field of the Invention

This invention relates to an aqueous solution of nitroglycerin.

2. Description of the Prior Art

Nitroglycerin, which has been used as a medicine against angina pectoris for more than 100 years, is still an important medicine for curing circulatory diseases, such as angina pectoris, cardiac asthma, and cerebral anemia due to local angiospasm. Although this medicine has usually been used in the form of a tablet, much attention has recently come to be directed to the use thereof in the form of an injectable solution which permits easier control of each dose, as it has begun to be employed for treating cardiac infarction or unsufficiency, and for hypotensive anesthesia during a surgical operation.

Various methods have hitherto been proposed for preparing an injectable solution of nitroglycerin, i.e., an aqueous solution thereof [Ho-Leung Fung, Am. J. Hosp. Pharm., vol. 35, 528 (1978)]. For example, the following methods are known:

(1) Water is added to a solution of nitroglycerin in ethanol or propylene glycol to form an aqueous solution of nitroglycerin;

(2) Lactose powder is caused to adsorb nitroglycerin, and dissolved in water;

(3) A commercially available sublingual tablet of nitroglycerin is dissolved in water, and insoluble impurities are removed by filtration; and (4) Nitroglycerin is directly dissolved in water.

The method as indicated at (1) above, however, involves a number of disadvantages which are due to the presence of ethanol or propylene glycol. Due to its decomposition caused by such an organic solvent, nitroglycerin has a low degree of stability for storage which makes it difficult to guarantee the quality of the injectable solution. The presence of such a solvent also complicates the pattern in which the medicine takes effect.

Referring to the method as indicated at (2) above, nitroglycerin in this method has a low degree of stability for storage due to the presence of lactose. Moreover, it is difficult to obtain any lactose warranted for the absence of any pyrogen and the presence of antigenicity, since the lactose according to the Japanese Pharmacopoeia is intended for internal or external use, and not for injection. Therefore, it is difficult to prepare an injectable solution of nitroglycerin by using any commercially available lactose.

The method (3) above is not a method which is suitable for manufacturing an injectable solution of nitroglycerin on an industrial basis. The use of a commercial end product as starting material leads to an increase in the cost of manufacture. It is not possible to avoid the inclusion of an ingredient or ingredients of the tablet which are not approved for use in an injection; therefore, nitroglycerin has a low degree of stability for storage when this method is used to prepare the injectable solution. Moreover, it is impossible to avoid the possibility of any pyrogen being included in the injectable solution.

As opposed to these methods, the method (4) above can be employed for preparing an injectable solution in which nitroglycerin maintains a satisfactory degree of stability for storage. As nitroglycerin is a highly explosive substance, however, it is impossible to transport it to a place where medicines are manufactured. Moreover, as nitroglycerin is not easily soluble in water, it is likely to explode during its dissolution, and a long time is required for the complete dissolution of nitroglycerin in water. This is definitely a factor which may result in promoting inclusion of any pyrogen which must be avoided for the manufacture of an intravenous injectable solution.

SUMMARY OF THE INVENTION

The inventors of this invention have made an extensive study for developing an aqueous solution of nitroglycerin which has a high degree of stability for storage, is easy to handle during its manufacture, and is suitable for use as an injectable solution. As the result, they have discovered that the aforesaid requirements can be satisfied by an aqueous solution of nitroglycerin comprising at least one substance selected from among sorbitol, mannitol and xylitol, in addition to nitroglycerin, and have accomplished this invention.

DETAILED DESCRIPTION OF THE INVENTION

This invention is concerned with an aqueous solution of nitroglycerin comprising at least one substance selected from among sorbitol, mannitol and xylitol, in addition to nitroglycerin, and having a high degree of stability for storage.

The aqueous solution of this invention has a pH value of 3 to 8, preferably 3.5 to 6. It contains 0.1 to 1 mg/ml, preferably 0.25 to 0.6 mg/ml, of nitroglycerin, and 25 to 150 mg/ml, preferably 40 to 100 mg/ml, of at least one substance selected from among sorbitol, mannitol and xylitol. It is mainly used as an injectable solution.

Sorbitol, mannitol and xylitol, of which at least one is used for this invention, are all highly safe substances the use of which is officially permitted for preparing an injectable solution.

In order to prepare an aqueous solution according to this invention, nitroglycerin is first dissolved in a highly volatile organic solvent, such as methanol, ethanol and acetone, to form a solution containing 1 to 10 W/V % of nitroglycerin. This solution is uniformly mixed with at least one substance in powdered form selected from among sorbitol, mannitol and xylitol. The mixture is dried at a temperature of 30° C. to 60° C., preferably 35° C. to 50° C., for volatilizing the organic solvent, whereby a powder containing 0.06 to 4% by weight of nitroglycerin adsorbed therein is obtained. The powder thus obtained is gradually dissolved in water while it is being stirred, whereby an aqueous solution of nitroglycerin is obtained. The pH of the solution can be adjusted as required.

The aqueous solution of nitroglycerin as hereinabove described can be prepared without involving any danger of explosion, and maintains a high degree of stability for a long period of time. an injectable solution can be prepared from this aqueous solution, if all the insoluble substances are removed therefrom by filtration, and the filtrate is sterilized by heating three times at 80° C. in an ampule, or by filtration through a GS type millipore filter or the like, followed by filling in a colored ampule. the injectable solution may be used directly, or after it is mixed with an infusion solution.

Reference will now be made to experiments showing the long-lasting stability of the aqueous nitroglycerin solution according to this invention, and the freedom of the aforementioned powder containing adsorbed nitroglycerin from any danger of explosion.

EXPERIMENT 1—Test (1) for Aqueous Nitroglycerin Solutions on Stability for Storage (Acceleration Test)

1. Preparation of Sample Solutions

Powders containing nitroglycerin adsorbed therein were prepared in accordance with the prescriptions shown in TABLE 1 by following the procedures set forth in EXAMPLE 1 below. Each powder was dissolved in distilled water for injection use, and the solution thus obtained was filled in an ampule, whereby Samples 1 to 3 of the solution according to this invention, and Control Samples 4 to 9 were prepared. At the same time, nitroglycerin was dissolved directly in different kinds of solvents, and each solution thus obtained was filled in an ampule, whereby Control Samples 10 to 12 were prepared.

2. Test Method

Each of the samples prepared as hereinabove described was stored at 79.6° C. for 10 days, and 96.5° C. for four days. Then, the amount of nitroglycerin remaining in each sample was determined by high-speed liquid chromatography.

3. Test Results

The test results are shown in TABLE 1.

As shown in TABLE 1, Control Sample #4 showed the maximum percentage of 88.7% and 67.7% of residual nitroglycerin in both of the cases, i.e., when stored at 79.6° C. for 10 days, and at 96.5° C. for four days, respectively, as far as the control samples prepared by using adsorbents were concerned. It is noted that it is impossible to use sodium ascorbate or urea as an adsorbent, because nitroglycerin is completely decomposed as found in Control Samples #7 and #9.

TABLE 1

| Sample | Prescription Nitroglycerin | Adsorbent | Solvent | Residual nitroglycerin (%) 79.6° C. 10 days | 96.5° C. 4 days |
|---|---|---|---|---|---|
| Invention | | | | | |
| 1 | 0.5 mg/ml | D-mannitol 50 mg/ml | Water | 94.1 | 83.2 |
| 2 | 0.5 mg/ml | D-sorbitol 50 mg/ml | " | 92.8 | 83.1 |
| 3 | 0.5 mg/ml | Xylitol 50 mg/ml | " | 93.1 | 82.9 |
| Control Sample | | | | | |
| 4 | 0.5 mg/ml | D-lactose (monohydrate) 50 mg/ml | Water | 88.7 | 67.7 |
| 5 | 0.5 mg/ml | Anhydrous dextrose 50 mg/ml | " | 83.7 | 59.5 |
| 6 | 0.5 mg/ml | L-lysine hydrochloride 50 mg/ml | " | 67.5 | 41.3 |
| 7 | 0.5 mg/ml | Sodium ascorbate (pH 5.5) 50 mg/ml | " | 0.0 | 0.0 |
| 8 | 0.5 mg/ml | Citric anhydride 16.8 mg/ml & sodium hydrogenphosphate 32.1 mg/ml | " | 80.3 | 61.9 |
| 9 | 0.5 mg/ml | Urea 16.3 mg/ml | " | 0.0 | 0.0 |

TABLE 1-continued

| Sample | Prescription Nitroglycerin | Adsorbent | Solvent | Residual nitroglycerin (%) 79.6° C. 10 days | 96.5° C. 4 days |
|---|---|---|---|---|---|
| 10 | 0.5 mg/ml | — | " | 95.2 | 83.0 |
| 11 | 5 mg/ml | — | Ethanol | 12.6 | — |
| 12 | 5 mg/ml | — | Propylene glycol | 64.8 | — |

Referring to the samples obtained by dissolving nitroglycerin directly in a solvent without the aid of any adsorbent, it is noted that neither ethanol nor propylene glycol is suitable for use as a solvent for preparing a nitroglycerin solution, because nitroglycerin is decomposed to a large extent as found in Control Samples #11 and #12 obtained by using ethanol and propylene glycol, respectively, and which showed a residual nitroglycerin percentage of 12.6% and 64.8%, respectively, after they had been stored at 79.6° C. for 10 days.

The samples of this invention prepared by using mannitol, sorbitol and xylitol as an adsorbent showed a residual nitroglycerin percentage of about 93 to 94%, and about 83% when stored at 79.6° C. for 10 days, and 96.5° C. for four days, respectively. These results indicate that the aqueous solution of nitroglycerin according to this invention maintains a high degree of stability for storage.

EXPERIMENT 2—Test (2) for Aqueous Nitroglycerin Solutions on Stability for Storage

1. Test Method

Samples 1 to 3 of this invention as used in EXPERIMENT 1 were stored at room temperature (25° C.) for three months and 8.5 months, respectively, and the amount of nitroglycerin remaining in each sample was determined by highspeed liquid chromatography.

2. Test Results

The test results are shown in TABLE 2 below.

TABLE 2

| Sample | Conditions of storage 25° C., 3 months | 25° C., 8.5 months |
|---|---|---|
| 1 | 99.9% | 99.7% |
| 2 | 99.9% | 99.7% |
| 3 | 99.8% | 99.7% |

As is noted from TABLE 2, all the samples of this invention showed a residual nitroglycerin percentage of 99.7% after they had been stored at 25° C. for 8.5 months. These results indicate that the aqueous nitroglycerin solution of this invention maintains a high degree of stability for storage over a long period of time without undergoing any appreciable decomposition of nitroglycerin.

EXPERIMENT 3—Test for Powder Containing Adsorbed Nitroglycerin on Stability against Explosion

1. Preparation of Samples

Sample powders containing nitroglycerin adsorbed therein according to this invention were prepared in accordance with the procedures set forth in EXAMPLE 1 by using (1) mannitol, (2) sorbitol and (3) xylitol as an adsorbent. Control Sample #4 was prepared solely from nitroglycerin without using any adsorbent.

2. Test Method

Drop hammer sensitivity tests were conducted by a sliding tester with a drop hammer weight of 5 kg.

3. Test Results

The test results are shown in TABLE 3.

TABLE 3

| Sample | Adsorbent Concentration of nitroglycerin | Sensitivity | Result |
| --- | --- | --- | --- |
| Invention | | | |
| 1 | Mannitol 1.13% | 3 to 5 | Slightly decomposed |
| 2 | Sorbitol 1.13% | 3 to 5 | Slightly decomposed |
| 3 | Xylitol 1.13% | 3 to 5 | Slightly decomposed |
| Control Sample | | | |
| 4 | — 100% | 1 to 2 | Completely exploded |

As is noted from TABLE 3, the control sample composed solely of nitroglycerin showed a sensitivity grade of 1 to 2, and was evaluated as having undergone complete explosion, but all the samples according to this invention showed a sensitivity grade of 3 to 5, and was evaluated as having undergone only slight decomposition. These results indicate that while nitroglycerin itself is a highly explosive substance, the powder containing adsorbed nitroglycerin as employed for this invention involves virtually no danger of explosion.

The samples were also subjected to a friction sensitivity test and an explosion test. The samples of this invention were found to be insensitive to friction as the result of the former test, and did not show any explosion during the latter test, as was the case with the adsorbents per se containing no nitroglycerin adsorbed therein.

The experiments as hereinabove described clearly show that the aqueous nitroglycerin solution of this invention has a high degree of stability for storage, and is easy to manufacture on an industrial basis.

A method of preparing an aqueous solution of nitroglycerin according to this invention will now be described more specifically with reference to examples.

EXAMPLE 1

0.2 kg of nitroglycerin was dissolved in 3.8 kg of ethanol to prepare 4 kg of a 5% nitroglycerin solution. This solution was uniformly mixed with 17.5 kg of D-mannitol powder. The powder was, then, dried at 40° C. by a hot air drier for volatilizing the ethanol to yield 17.7 kg of D-mannitol powder containing nitroglycerin adsorbed therein. Then, 386 kg of distilled water for injection use were placed in a still having a volume of 1 ton, and while it was being stirred at a high speed, the powder containing nitroglycerin was gradually dissolved in the distilled water over about one hour, whereby an aqueous solution containing about 0.5 mg/ml of nitroglycerin was obtained. The solution thus obtained had a pH value of 4.7.

EXAMPLE 2

The procedures of EXAMPLE 1 were repeated for preparing an aqueous solution of nitroglycerin, except that D-sorbitol was used instead of D-mannitol. The solution thus obtained had a pH vaklue of 4.3.

EXAMPLE 3

The procedures of EXAMPLE 1 were repeated again for preparing an aqueous solution of nitroglycerin, except that D-xylitol was used instead of D-mannitol. The solution thus obtained had a pH value of 4.3.

REFERENCE EXAMPLE 1

The aqueous solution of nitroglycerin prepared in accordance with the procedures of EXAMPLE 1 was sterilized by filtration through a GS type millipore filter having a mesh size of 0.22 μm. About 10.6 ml of the sterilized solution were filled in each of a number of 10-ml brown ampules, whereby there was obtained an injectable solution containing about 5 mg of nitroglycerin per ampule.

What is claimed is:

1. An aqueous solution of nitroglycerin comprising: an amount of nitroglycerin in the range 0.1 to 1.0 mg of nitroglycerin per milliliter of said solution; and an amount of a component consisting of at least one substance selected from the group consisting of sorbitol, mannitol and xylitol in the range 25 to 150 mg of said component per milliliter of said solution, said solution having a pH value of 3 to 8.

2. An aqueous solution of nitroglycerin as set forth in claim 1, containing 40 to 100 mg of said component per milliliter.

3. An aqueous solution of nitroglycerin as set forth in claim 1, containing 0.25 to 0.6 mg of nitroglycerin per milliliter.

4. An aqueous solution of nitroglycerin comprising: an amount of nitroglycerin in the range 0.25 to 0.6 mg of nitroglycerin per milliliter of said solution; and an amount of a component consisting of at least one substance selected from the group consisting of sorbitol, mannitol and xylitol in the range 40 to 100 mg of said component per milliliter of said solution, said solution having a pH value of 3 to 8.

* * * * *

UNITED STATES PATENT AND TRADEMARK OFFICE
CERTIFICATE OF CORRECTION

PATENT NO. : 4,323,577
DATED : April 6, 1982
INVENTOR(S) : Takaaki Ohkuma et al.

It is certified that error appears in the above-identified patent and that said Letters Patent is hereby corrected as shown below:

Add Claim 5 as follows:

-- 5. An intravenous injectable solution of nitroglycerin comprising 0.25 to 0.6 mg. of nitroglycerin and 40 to 100 mg of mannitol per milliliter, and having a pH value of 3 to 8. --.

On The Title Page, "4 Claims" should read -- 5 Claims --.

Signed and Sealed this

Seventeenth Day of August 1982

[SEAL]

Attest:

GERALD J. MOSSINGHOFF

Attesting Officer    Commissioner of Patents and Trademarks